United States Patent [19]

Alburn et al.

[11] 3,976,692

[45] Aug. 24, 1976

[54] AMIDES OF 1-AMINOCYCLO-PENTANECARBOXYLIC ACID

[75] Inventors: Harvey E. Alburn, West Chester; Norman H. Grant, Wynnewood, both of Pa.

[73] Assignee: American Home Products Corporation, New York, N.Y.

[22] Filed: Mar. 21, 1975

[21] Appl. No.: 560,896

Related U.S. Application Data

[63] Continuation-in-part of Ser. No. 408,137, Oct. 19, 1973, abandoned, which is a continuation of Ser. No. 209,427, Dec. 17, 1971, abandoned.

[52] U.S. Cl. .......................... 260/557 R; 260/514 J; 260/546; 260/563 P; 424/320
[51] Int. Cl.² ........................................ C07C 103/19

[58] Field of Search ............................... 260/557 R

[56] References Cited

UNITED STATES PATENTS

| | | | |
|---|---|---|---|
| 3,206,455 | 9/1965 | Alburn et al. | 260/239.1 |
| 3,304,167 | 2/1967 | Buntin et al. | 71/99 |
| 3,641,149 | 2/1972 | Edgerton | 260/557 R |

*Primary Examiner*—Daniel E. Wyman
*Assistant Examiner*—Thomas A. Waltz
*Attorney, Agent, or Firm*—Stephen Venetianer

[57] ABSTRACT

The compounds are amides of 1-aminocyclopentanecarboxylic acid, having valuable pharmacodynamic properties in that they possess analgesic activity in warm-blooded animals.

3 Claims, No Drawings

AMIDES OF 1-AMINOCYCLO-PENTANECARBOXYLIC ACID

This is a continuation-in-part of application Ser. No. 408,137 filed Oct. 19, 1973 now abandoned which is a continuation of application Ser. No. 209,427 filed Dec. 17, 1971, now abandoned.

DESCRIPTION OF THE INVENTION

This invention relates generally to novel chemical compounds having valuable pharmacodynamic properties and to processes for preparing said compounds. The novel compounds of the invention are the amides of 1-aminocyclopentanecarboxylic acid encompassed within the following general formula:

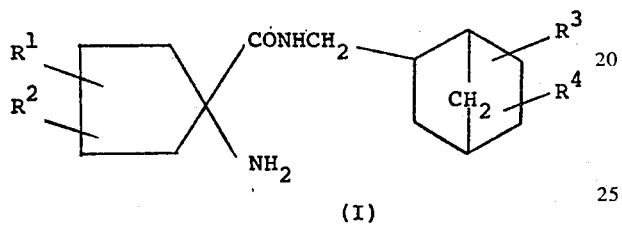

(I)

wherein $R^1$, $R^2$, $R^3$ and $R^4$ are each selected from the group consisting of hydrogen, lower alkyl, lower alkoxy, hydroxy, halogen, and nitro, and each of $R^3$ and $R^4$ may additionally be amino; and the pharmaceutically-acceptable acid-addition salts thereof.

Preferred compounds are of the following formula:

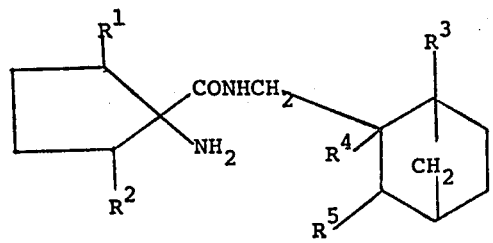

wherein $R^1$ and $R^2$ are each selected from the group consisting of hydrogen, lower alkyl, lower alkoxy, hydroxy, halogen and nitro, with the proviso that either $R^1$ or $R^2$ is always hydrogen; $R^3$, $R^4$ and $R^5$ are each selected from the group consisting of lower alkyl and hydrogen, with the proviso that two of $R^3$, $R^4$ and $R^5$ are always hydrogen and the pharmaceutically-acceptable acid-addition salts therof.

Other preferred compounds are of the formula:

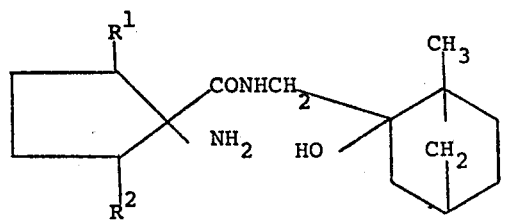

wherein $R^1$ and $R^2$ have the same significance as above.

The novel compounds of formula (I) may conveniently be prepared by heat-reacting a selected N-carboxyanhydride of 1-aminocyclopentanecarboxylic acid with an endo-2-aminomethylbicycloheptane in accordance with the following reaction scheme:

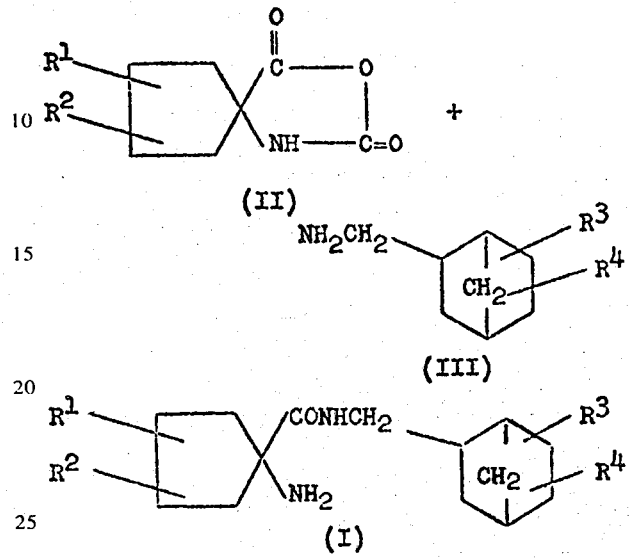

wherein $R^1$, $R^2$, $R^3$ and $R^4$ have the same meaning described hereinbefore.

The reactants (III), the suitable derivatives of endo-2-aminomethylbicycloheptane, employed in the preparative process illustrated by the above reaction scheme may readily be prepared by known synthesis for adding the desired substituents in the ring of endo-2-aminomethylbicycloheptane per se. The reactants (II), the N-carboxyanhydrides of 1-aminocyclopentanecarboxylic acid, which are not commercially available, can easily be prepared in accordance with standard organic procedures well known to those skilled in the art. For example, a procedure which has been employed to synthesize the anhydrides of formula (II) above utilized in the preparation of compound (I) of the present invention, is described in U.S. Pat. No. 3,206,455, "Process for Producing 6-(α-aminoacylamino) Penicillanic Acids", H. E. Alburn and N. H. Grant.

It has been discovered that compounds of formula (I) meeting the described qualifications have valuable pharmacologic properties. More specifically, said compounds have been found to have unexpected analgesic activity, as referred to in greater detail hereinafter.

The analgesic activity of composition within the purview of the present invention has been demonstrated by following a modification of the test procedure described by Eddy and Leinbach in Journal of Pharmacology 107:385 (1935), an accepted test for analgesic agents. In this test, rats are administered the compound orally, intraperitoneally or intramuscularly and the time required for a hind leg response to a pain stimulus caused by heat is measured. Thus, the compounds of the invention exhibit analgesic activity in rats at a dosage of from 50 mg. to 200 mg. per kilogram of body weight orally and intraperitoneally and from 25 mg. to 150 mg. per kilogram of body weight intramuscularly.

In the exercising of the method of the invention, the compounds of Formula I used therein may be administered alone or in combination with pharmaceutically acceptable carriers, and the proportion of which is determined by the solubility and chemical nature of the compound selected, the chosen route of administration, and standard pharmaceutical practice. For example, they may be administered orally in the form of tablets or capsules, which may contain conventional excipients, or in the form of solutions; or they may be injected parenterally, that is, intramuscularly, intravenously or subcutaneously. For parenteral administration, they may be used in the form of sterile solutions containing other solutes, for example, enough saline or glucose to make the solutions isotonic.

The dosage of the present therapeutic agents will vary with the form of administration and the particular compound chosen. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The following examples are illustrative of the preparation of the compounds useful in the method of the invention and of the exercising of the latter, but are not to be considered necessarily limitative thereof:

EXAMPLE I

1-Amino-N-(norbornan-2-ylmethyl)cyclopentanecarboxamide

Five grams of endo-2-aminomethylbicycloheptane hydrochloride was stirred in 100 ml. of pyridine until the solute dissolved. There was then added 4.35 g of N-carboxy-1-aminocyclopentanecarboxylic acid anhydride (NCA), and then the mixture was allowed to stand overnight at room temperature. Assay by formation of the hydroxamate showed 12 mg. ml. of intact NCA. The mixture was therefore refluxed for 1.5 hour, whereupon all the NCA reacted. The system was concentrated in vacuo, 200 ml. of water was added, and evaporation was repeated. There was then added 100 ml. of absolute ethanol, resulting in complete solution. This was followed by addition of 3 ml. of concentrated HCl, and the system was taken to dryness. The residue was extracted under reflux into 325 ml. of acetone. On chilling, the desired product precipitated.

Calcd. for $C_{14}H_{24}N_2O$ HCl : C, 61.6; H, 9.2; Cl, 13.0
Found: C, 59.4; H, 9.1; Cl, 12.7.

The product possesses analgesic activity, as shown in the test referred to hereinbefore.

EXAMPLE II

Following the procedure of Example I, a series of N-carboxy anhydrides of substituted 1-aminocyclopentanecarboxylic acids (II) are reacted with selected derivatives of endo-2-aminomethylbicycloheptanes (III) to prepare the amides of 1-aminocyclopentanecarboxylic acids (I) of the invention, which have analgesic activity in warm-blooded animals as demonstrated by the standard pharmacological procedure described hereinbefore. The reactants (II) and (III) and resulting compounds (I) of the invention having said activity are set forth in the table below:

Table

| N-carboxy Anhydride of 1-Amino-cyclopentanecarboxylic acid (II) | Substituted endo-2-aminomethyl-bicycloheptane (III) | Resulting Amide (I) |
| --- | --- | --- |
| N-carboxy-2-bromo-1-aminocyclo-pentanecarboxylic acid | 5-chloro-endo-2-aminomethylbi-cycloheptane | 2-bromo-1-amino-N-(5-chloro-norbornan-2-ylmethyl)cyclo-pentanecarboxamide |
| N-carboxy-2-methyl-1-aminocyclo-carboxylic acid | 5-amino-endo-2-aminomethylbi-cycloheptane | 2-methyl-1-amino-N-(5-amino-norbornan-2-ylmethyl)cyclopen-tanecarboxamide |
| N-carboxy-1-aminocyclopentane-carboxylic acid | 5,6-dimethyl-endo-2-amino-methylbicycloheptane | 1-amino-N-(5,6-dimethyl-nor-bornan-2-ylmethyl)cyclopentane-carboxamide |
| N-carboxy-2-nitro-1-aminocyclo-carboxylic acid | 3-methoxy-endo-2-amino-methylbicycloheptane | 2-nitro-1-amino-N-(3-methoxy-norbornan-2-ylmethyl)cyclopen-tanecarboxamide |
| N-carboxy-2-chloro-3-propoxy-1-aminocyclopentanecarboxylic acid | 5-propyl-6-amino-endo-2-aminomethylbicycloheptane | 2-chloro-3-propoxy-1-amino-N-(5-propyl-6-amino-norbornan-2-ylmethyl)cyclopentanecarboxamide |
| N-carboxy-3-propyl-1-aminocyclo-carboxylic acid | 5-propoxy-endo-2-aminomethyl-bicycloheptane | 3-propyl-1-amino-N-(5-propoxy-norbornan-2-ylmethyl)cyclopen-tanecarboxamide |
| N-carboxy-2-methoxy-3-fluoro-1-aminocyclopentanecarboxylic acid | 3-hydroxy-endo-2-aminomethylbi-cycloheptane | 2-methoxy-3-fluoro-1-amino-N-(3-hydroxy-norbornan-2-ylmethyl)-cyclopentanecarboxamide |
| N-carboxy-3-hydroxy-1-aminocyclo-pentanecarboxylic acid | 3,5-dibromo-endo-2-aminomethyl-bicycloheptane | 3-hydroxy-1-amino-N-(3,5-dibromo-norbornan-2-ylmethyl)cyclopentane-carboxamide |

We claim:
1. An amide of 1-aminocyclopentanecarboxylic acid selected from those compounds having the formula:

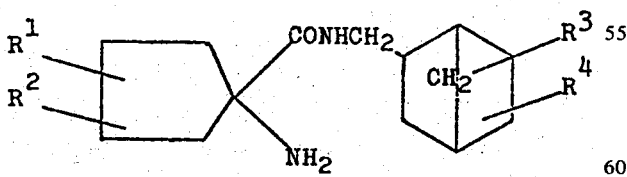

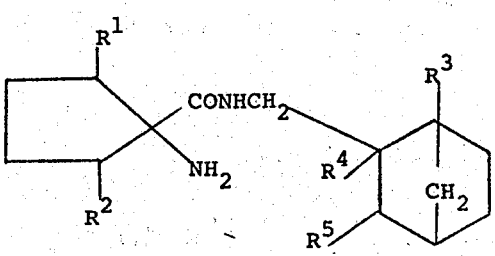

wherein $R^1$ and $R^2$ are each selected from the group consisting of hydrogen, lower alkyl, lower alkoxy, hydroxy, and nitro, with the proviso that either $R^1$ or $R^2$ is always hydrogen; $R^3$, $R^4$ and $R^5$ are each selected from the group consisting of lower alkyl and hydrogen, with the proviso that two of $R^3$, $R^4$ and $R^5$ are always hydrogen and the pharmaceutically-acceptable acid-addition salts thereof.

2. A compounds as defined in claim 1 which is 1-amino-N (norbornan-2-ylmethyl)cyclopentanecarboxamide.

3. A compound having the following formula:

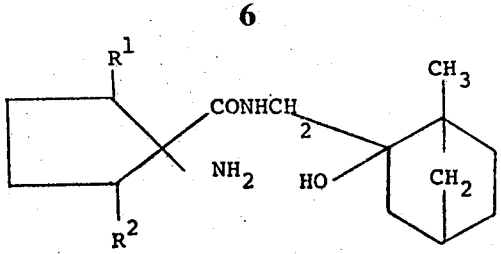

wherein $R^1$ and $R^2$ have the same significance as in claim 1.

* * * * *